United States Patent [19]

Ilsink

[11] Plant 5,082

[45] Aug. 9, 1983

[54] ROSE PLANT JP-593

[75] Inventor: G. Peter Ilsink, Doorn, Netherlands

[73] Assignee: Jackson & Perkins Co., Medford, Oreg.

[21] Appl. No.: 323,672

[22] Filed: Nov. 20, 1981

[51] Int. Cl.[3] ..... A01H 5/00

[52] U.S. Cl. ..... Plt./9

[58] Field of Search ..... Plt./9

*Primary Examiner*—James R. Feyrer

*Attorney, Agent, or Firm*—Klarquist, Sparkman, Campbell, Leigh, Whinston & Dellett

[57] ABSTRACT

A miniature rose variety consisting of a compact plant, profusely branched; with abundant foliage; medium pink flowers; and light, daisy-like fragrance.

1 Drawing Figure

This present invention relates to a new and distinct variety of rose plant of the miniature class which was originated by me by crossing the variety Marlena with an unnamed variety.

The primary objective of this breeding was to produce a new rose variety of the miniature class, useable landscape plantings such as foundation plantings, free of disease, easy to keep in orderly shape, and bearing freely of pink blooms. This objective was substantially achieved along with other desirable improvements as evidenced by the following unique combination of characteristics which are outstanding in the new variety and which distinguish it from its parents as well as from all other varieties of which I am aware:

1. A compact plant, rarely over 24" in height, profusely branched.
2. Medium green foliage, abundantly covering the plant.
3. Strong resistance to rose powdery mildew.
4. Medium pink flowers of approximately 15 petals.
5. Very light, daisy-like fragrance of the blooms.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated.

Parentage:

*Seed parent.*—Unknown.

*Pollen parent.*—Marlena Seedling.

Classification:

*Botanical.*—Rosa hybrid.

*Commercial.*—Miniature.

FLOWER

Observations made from specimens grown in a greenhouse at Irvine, Calif. in January.

Blooming habit: Continuous.

Bud:

*Size.*—$\frac{3}{8}$" to $\frac{1}{2}$" when petals start to unfurl.

*Form.*—Pointed ovoid, broad base.

*Color.*—When sepals first divide, Pink from Red Group 55A; when half blown, upper side of petals Pink from Red Group 55A, lower side of petals Pink from Red Group 55B.

*Sepals.*—Color: Outer surface Green 138A, lightly shaded with brownish tones; lightly pubescent; three appendaged sepals heavily appendaged; two unappendaged sepals hairy edged.

*Receptacle.*—Color: Green 138A. Shape: Funnel. Size: Large. Surface: Pubescent.

*Peduncle.*—Length: Medium. Surface: Glandular and lightly pubescent. Color: Light green, bronzy. Strength: Stiff, erect.

*Opening.*—Petals fold outward and remain flat.

Bloom:

*Size.*—Medium. Average open size $1\frac{1}{4}$".

*Borne.*—In clusters, flat.

*Stems.*—Medium, strong.

*Form.*—When first open, flat. Permanence: Retains its form to the end.

*Petalage.*—Number of petals under normal conditions: approximately 15.

*Color.*—Center of flower: Upper side of petals Pink 55A. Reverse side of petals Pink from Red Group 55A. Base of petals Light Yellow at point of attachment. General tonality from a distance Pink 55A.

*Variegations.*—Occasional whitish streaks at midrib of some petals.

*Discoloration.*—General tonality at end of first day, Pink 55A; third day, Pink, fading to 55C.

*Fragrance.*—Slight, daisy-like.

Petals:

*Texture.*—Thin.

*Shape.*—Obovate.

*Form.*—Flat.

*Arrangement.*—Imbricated. Petaloids in center, few.

*Persistence.*—Drop off cleanly.

*Lastingness.*—On the plant, long. As cut flower, long.

Reproductive parts:

*Anthers.*—Large. Color, yellow near 17B. Arrangement, regular around styles.

*Filaments.*—Color: Green-Yellow 1D.

*Pollen.*—Gold yellow.

*Styles.*—Color: Reddish/White.
*Stigmas.*—Color: White.

PLANT

Form: Miniature bush.
Growth: Vigorous, upright, branching, compact.
Foliage: Number of leaflets on normal mid-stem leaves: 5 to 7.
*Size.*—Medium.
*Quantity.*—Normal.
*Color.*—New foliage: Green near 137D. Old foliage: Green near 137C.
Leaflets:
*Shape.*—Oval pointed.
*Texture.*—Upper side — semi-glossy.
*Edge.*—Serrated.
*Serration.*—Small.
*Petiole.*—Rachis: Color, green. Underside: prickles.
*Stipules.*—Long, bearded.

*Disease resistance.*—Resistant to mildew under normal growing conditions at Irvine, Calif.
Wood:
*New wood.*—Color: Light green. Bark: Smooth.
*Old wood.*—Color: Green. Bark: Smooth.
Prickles:
*Quantity.*—On main stalks from base, ordinary. On laterals from stalk, ordinary.
*Form.*—Narrow base, long, hooked downward.
*Color when young.*—Brown.
*Position.*—Irregular.
Small prickles:
*Quantity.*—On main stalks, none. On laterals, none.

I claim:

1. A new and distinct variety of rose plant of the miniature class, substantially as herein shown and described, characterized particularly as to novelty by the unique combination of its compact, dwarf plant, with mildew resistant foliage, bearing 15 petalled pink, slightly fragrant flowers.

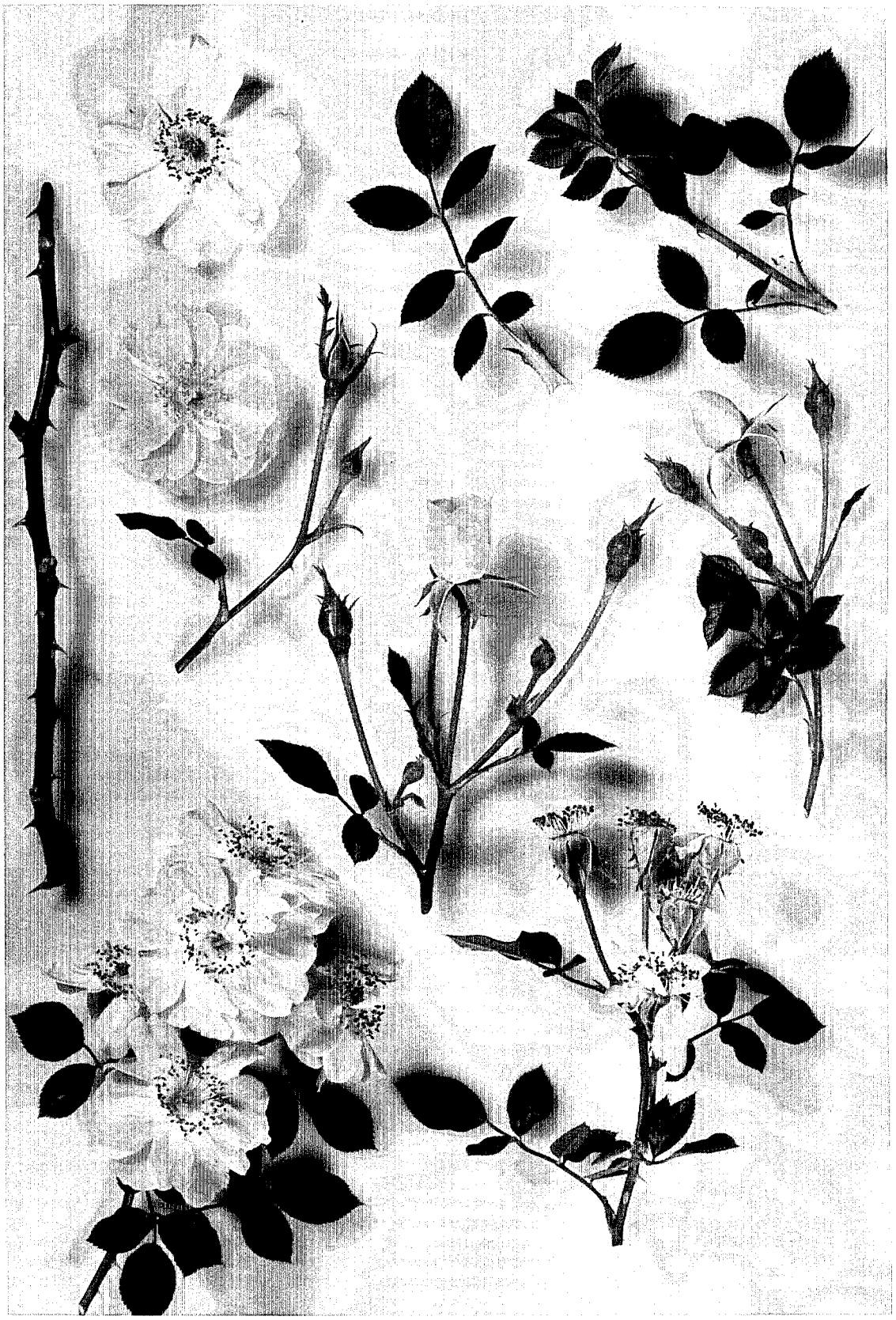

* * * * *